United States Patent [19]

Harder

[11] Patent Number: 4,948,722

[45] Date of Patent: Aug. 14, 1990

[54] PHOTOGRAPHIC MATERIAL AND PROCESS COMPRISING A PYRAZOLOAZOLE DYE-FORMING COUPLER

[75] Inventor: John W. Harder, Rochester, N.Y.

[73] Assignee: Eastman Kodak Company, Rochester, N.Y.

[21] Appl. No.: 265,155

[22] Filed: Oct. 31, 1988

[51] Int. Cl.$^5$ ................................................ G03C 7/38
[52] U.S. Cl. ...................................... 430/558; 430/546
[58] Field of Search ................ 430/558, 386, 387, 546

[56] References Cited

U.S. PATENT DOCUMENTS

| | | | |
|---|---|---|---|
| 4,443,536 | 4/1984 | Lestina | 430/552 |
| 4,514,490 | 4/1985 | Seto et al. | 430/558 |
| 4,540,654 | 9/1985 | Sato et al. | |
| 4,639,413 | 1/1987 | Kawagishi et al. | 430/546 |
| 4,639,415 | 1/1987 | Kaneko et al. | 430/551 |
| 4,665,015 | 5/1987 | Iijima et al. | 430/543 |
| 4,755,455 | 7/1988 | Iwasa | 430/558 |

FOREIGN PATENT DOCUMENTS

| | | |
|---|---|---|
| 0284239 | 9/1988 | European Pat. Off. . |
| 0284240 | 9/1988 | European Pat. Off. . |
| 0285274 | 10/1988 | European Pat. Off. . |
| 1255343 | 11/1986 | Japan ............................. 430/558 |
| 1247493 | 9/1971 | United Kingdom . |
| 1252418 | 11/1971 | United Kingdom . |
| 1398979 | 6/1975 | United Kingdom . |

OTHER PUBLICATIONS

Hackh's Chemical Dictionary, 4th ed, J. Grant, p. 534.
Research Disclosure, Item No. 12443, Aug. 1974; *Research Disclosure*, Kenneth Mason Publications, Ltd., Hampshire, England.

*Primary Examiner*—Paul R. Michl
*Assistant Examiner*—Lee L. Wright
*Attorney, Agent, or Firm*—Richard E. Knapp

[57] ABSTRACT

Novel pyrazoloazole dye-forming couplers comprising (I) at least one polyether group (A) comprising at least two ether (—O—) groups and (II) having between the group (A) and the pyrazoloazole nucleus a linking group (L) that is capable of increasing the reactivity of the coupler to enable improved dye images in a photographic element and process. These couplers are useful in photographic silver halide elements and processes.

7 Claims, No Drawings

PHOTOGRAPHIC MATERIAL AND PROCESS COMPRISING A PYRAZOLOAZOLE DYE-FORMING COUPLER

This invention relates to novel pyrazoloazole dye-forming couplers and to photographic silver halide materials and processes using such couplers.

Color images are customarily obtained in the photographic art by reaction between the oxidation product of a silver halide developing agent and a dye-forming coupler. Pyrazolone couplers are useful for forming magenta dye images; however, pyrazoloazole couplers, particularly pyrazolotriazole couplers, represent another class of couplers that are useful for this purpose. Examples of pyrazolotriazole couplers, particularly pyrazolo-[3,2-c]-s-triazole couplers, are described in, for instance, U.S. Pat. No. 4,443,536; U.K. Patent Nos. 1,247,493; 1,252,418 and 1,398,979; and U.S Pat. Nos. 4,665,015; 4,514,490; 4,639,413; and 4,639,415. An example of such a pyrazolotriazole coupler is represented by the formula:

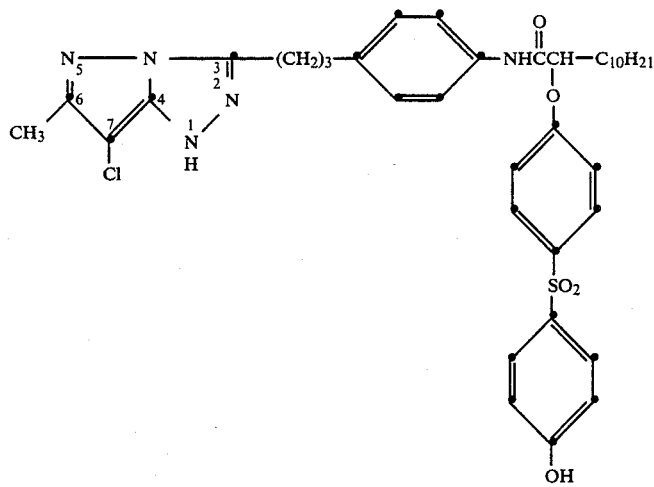

While such magenta couplers are useful in photographic silver halide materials and processes, many such couplers do not have sufficient coupler reactivity. It has been desirable to provide a pyrazoloazole coupler that has increased reactivity to provide increased maximum magenta image-dye density in color photographic silver halide materials and processes.

It has been found that a novel pyrazoloazole dye-forming coupler enabling the described advantages comprises (I) at least one polyether group (A) comprising at least two ether (—O—) groups and (II) having between the group (A) and the pyrazoloazole nucleus a linking group (L).

Such dye-forming couplers are particularly useful in photographic silver halide materials and processes.

Pyrazolotriazoles are particularly useful pyrazoloazoles as described. Such pyrazolotriazoles include, for example, a 1H-pyrazolo[2,3-b]-1,2,4-triazole or a 1H-pyrazolo[3,2-c]-s-triazole. A 1H-pyrazolo[2,3-b]-1,2,4-triazole can also be named as a 1H-pyrazolo[1,5-b]-1,2,4-triazole. The latter nonmenclature has neen used in the photographic art in, for example, U.S. Pat. No. 4,540,654. The group containing the polyether group (A) and the linking group as described in the case of a 1H-pyrazolo-[2,3-]-1,2,4-triazole is in the 2-and/or 6-position and in the case of a pyrazolo[3,2-c]-s-triazole in in the 6- and/or 3-positions.

It is believed that the combination of the polyether group (A) as described and the linking group enable a useful degree of water solubilization of the coupler that in turn enables the increased reactivity observed. The combination of these groups enables formation of higher maximum dye density from the coupler than is otherwise observed when only one of these groups is present on the pyrazoloazole nucleus of the coupler. The combination of the two groups enables tailoring of the reactivity of the coupler to a desired degree. For example, selection of the number of ether groups can be used to help tailor the degree of water solubility that the coupler has. The linking group on the other hand influences the polyether group and the coupler by enhancing the polar nature of the molecule, providing better reactivity with oxidized developer.

A typical pyrazoloazole coupler as described is represented by the formula:

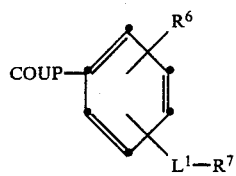

wherein

COUP is a pyrazoloazole coupler nucleus, preferably a pyrazolotriazole coupler nucleus;

$R^6$ is hydrogen or unsubstituted or substituted alkyl, such as alkyl containing 1 to 30 carbon atoms, for example methyl, ethyl, propyl, n-butyl and t-butyl; aryl, such as phenyl; alkoxy, such alkoxy containing 1 to 30 carbon atoms, such as methoxy, ethoxy, propoxy, and eicosyloxy; and aryloxy, such as phenoxy; and $L^1$ is —NHCO, —NHSO$_2$—, —NHPO—$R^{64}$, —NH-CONH—, —NHCO—$R^4$—, —NHSO$_2$—$R^4$—;

$R^4$ is unsubstituted or substituted alkylene, such as alkylene containing 1 to 2 carbon atoms, for example, methylene, ethylene, isopropylene,

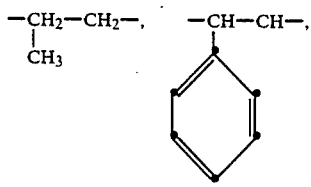

phenethyl and benzyl.

$R^{6a}$ is $R^6$ or $O-R^7$; and, $R^7$ is a polyether group, preferably a polyether group containing at least two $-OCH_2Ch_2-$ groups.

The linking group $L^1$ is preferably bonded directly to the the pyrazoloazole coupler nucleus at a non-coupling site. A highly preferred coupler is a pyrazolo[3,2-c]-s-triazole having the linking group in at least one of the 3- and 6-positions.

The polyether group can be terminated by any group that does not adversely affect the advantages of the coupler, for example an alkyl group, such as a methyl, ethyl, propyl, n-butyl, t-butyl or isopropyl, or aryl group, such as phenyl. It is often most useful to have the polyether group terminated by a water-solubilizing group, such as a carboxy, sulfonamide, alkyl alcohol, or phenol group.

An especially useful pyrazoloazole coupler as described is a pyrazolo[3,2-c]-s-triaxole having a group (B) in at least one of the 3- and 6-positions represented by the formula:

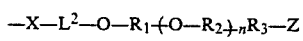

wherein n is 1 or 2;

X is a bond or unsubstituted or substituted alkylene, such as alkylene containing 1 to 25 carbon atoms, such as methylene, ethylene, or decylene; or arylene, such as unsubstituted or substituted phenylene;

$L^2$ is a linking group selected from the group consisting of $-NHCO-$; $-NHSO_2-$; $-NHCO-O-R^4-$, and $-NHCONH-R^4-$;

$R_1$, $R_2$, $R_3$, and $R^4$ are individually unsubstituted or substituted alkylene or arylene, as described; and Z is a water solubilizing group, such as carboxy, sulfonamide, alkyl alcohol, or phenol, or unsubstituted or substituted alkyl, such as alkyl containing 1 to 25 carbon atoms, for example, methyl, ethyl, propyl, n-butyl or t-butyl, or unsubstituted or substituted aryl, such as phenyl.

Illustrative examples of useful couplers containing described linking groups and polyether groups are as follows:

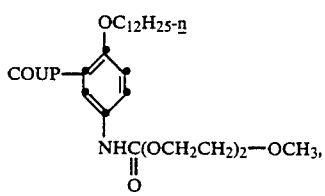

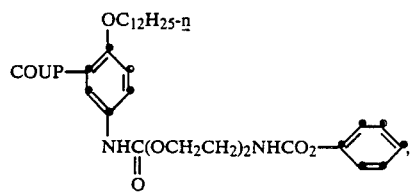

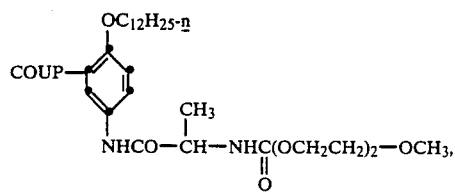

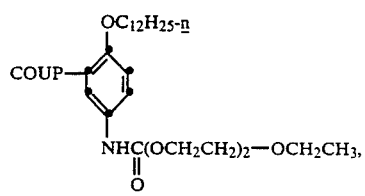

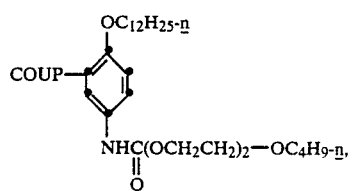

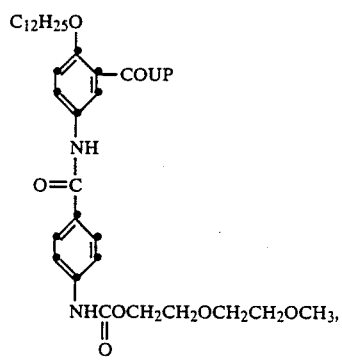

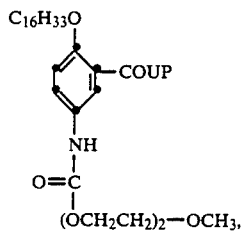

-continued

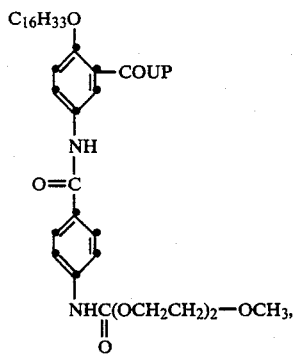

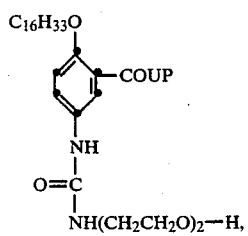

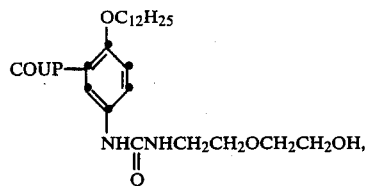

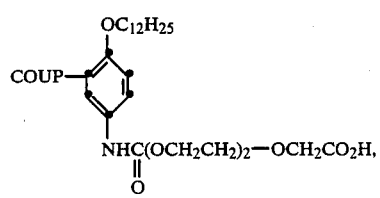

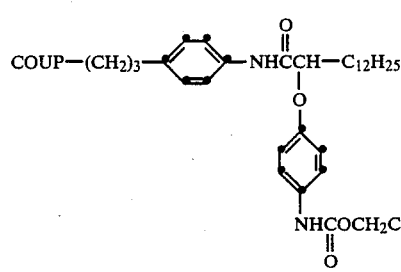

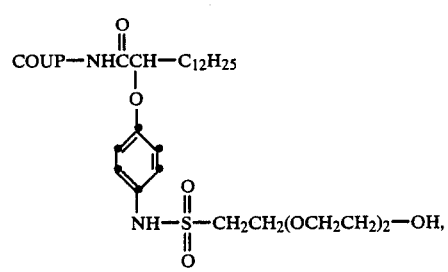

or

-continued

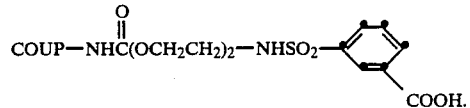

The pyrazoloazole coupler typically contains, in a position that does not contain the described polyether and linking groups, hydrogen or a group that typically promotes solubility, diffusion resistance or dye hue of the dye formed from upon reaction of the coupler with the oxidized color developing agent.

The pyrazoloazole coupler typically contains, in a position not containing the polyether and linking group, as described, hydrogen or a group selected from the following: amino, such as dioctylamino, dimethylamino, and dodecylamino; alkyl, such as alkyl containing 1 to 40 carbon atoms, for example methyl, ethyl, n-propyl, i-propyl, n-butyl, t-butyl, and dodecyl; cycloalkyl, such as cyclohexyl and cyclopentyl; aryl, such as aryl containing 6 to 30 carbon atoms, for example, phenyl, naphthyl and mesityl; carboxy; cyano; nitro; a heterocyclic group, such as a heterocyclic group comprised of atoms selected from carbon, oxygen, nitrogen, and sulfur atoms necessary to complete a five or six member ring, for example furyl, pyrrolyl, oxazolyl, thienyl, thiazolyl, and pyridyl; or $-(L_a)_w-(L_b)_q-R_{6c}$ wherein $L_a$ is a linking group that is the same as or different from the described linking groups and that does not adversely affect the desired properties of the coupler, such as an alkylene group, for example alkylene containing 1 to 20 carbon atoms, including methylene, ethylene, propylene, n-butylene, isopropylmethylene, and octylene, or arylene, for example, phenylene and naphthylene; $L_b$ is also a linking group that is the same as or different from the described linking groups and that does not adversely affect the desired properties of the coupler, and is typically O, S, $CO_2$, $SO_2$, SO, $NR_7CO$, $NR_7SO_2$, $CONR_7$, $NR_7SO_2NR_8$, $SO_2NR_7$, $O-CONR_7$, $NR_7CONR_8$ and $N_7CO-O$. $R_7$ and $R_8$ are individually hydrogen, alkyl, such as alkyl containing 1 to 30 carbon atoms, for example, methyl, ethyl, propyl, n-butyl, t-butyl and dodecyl, or aryl, such as aryl containing 6 to 30 carbon atoms, for example, phenyl and naphthyl; w and q are individually 0 or 1; and, $R_{6c}$ is alkyl, such as alkyl containing 1 to 30 carbon atoms, for example, methyl, ethyl, propyl, n-butyl, t-butyl and octyl, or aryl, such as aryl containing 6 to 30 carbon atoms, for example phenyl, naphthyl and mesityl; or a heterocyclic group, such as a five or six member heterocyclic group comprised of atoms selected from carbon, oxygen, nitrogen and sulfur atoms necessary to complete a five or six member heterocyclic ring, such as an oxazole, pyridine, pyrrole or thiophene ring.

These groups are unsubstituted or substituted with groups that do not adversely affect the desired properties of the pyrazoloazole coupler. Examples of useful substituents include ballast groups and coupler moieties that are known to be useful in the photographic art, or alkyl, such as alkyl containing 1 to 4 carbon atoms, for example, methyl, ethyl, and t-butyl.

The pyrazoloazole contains in the coupling position, hydrogen or a coupling-off group, also known as a leaving group.

Coupling-off groups are known to those skilled in the art. Such groups can determine the equivalency of the coupler, can modify the reactivity of the coupler, or can advantageously affect the layer in which the coupler is coated or other layers in the element by performing, after release from the coupler, such functions as development inhibition, development acceleration, bleach inhibition, bleach acceleration, color correction, and the like. Representative classes of coupling-off groups include halogen, particularly chlorine, bromine, or fluorine, alkoxy, aryloxy, heterocyclyloxy, sulfonyloxy, acyloxy, carbonamido, imido, acyl, heterocyclylimido, thiocyano, alkylthio, arylthio, heterocyclylthio, sulfonamido, phosphonyloxy and arylazo. They are described in, for example, U.S. Pat. Nos. 2,355,169; 3,227,551; 3,432,521; 3,476,563; 3,617,291; 3,880,661; 4,052,212 and 4,134,766; and in U. K. patents and published application Nos. 1,466,728; 1,531,927; 1,533,039; 2,006,755A and 2,017,704A; the disclosures of which are incorporated herein by reference.

Examples of specific coupling-off groups are

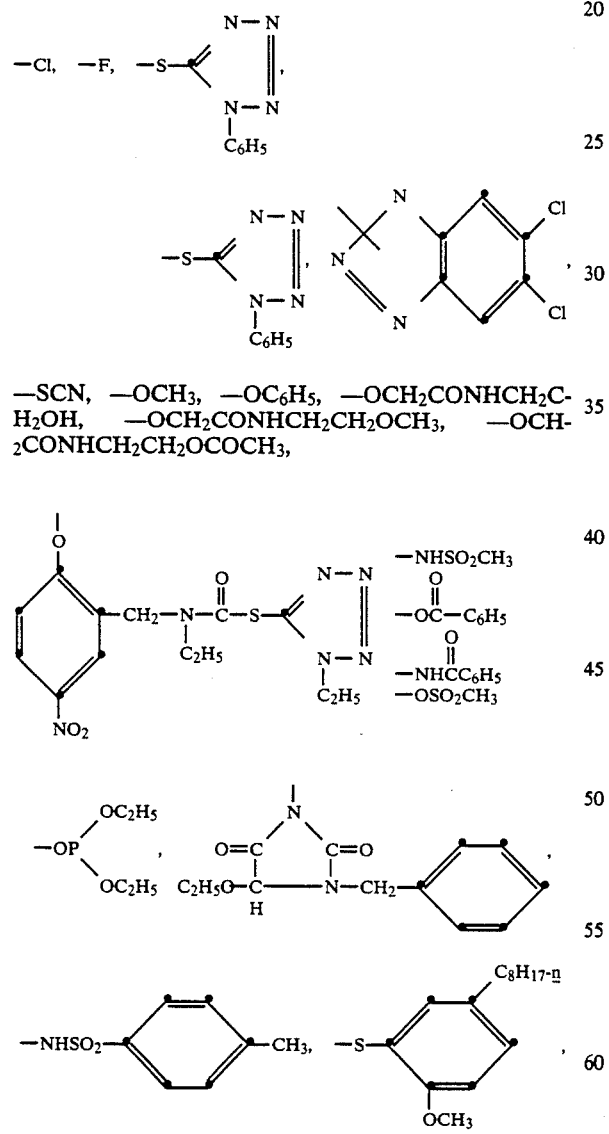

—SCN, —OCH$_3$, —OC$_6$H$_5$, —OCH$_2$CONHCH$_2$CH$_2$OH, —OCH$_2$CONHCH$_2$CH$_2$OCH$_3$, —OCH$_2$CONHCH$_2$CH$_2$OCOCH$_3$,

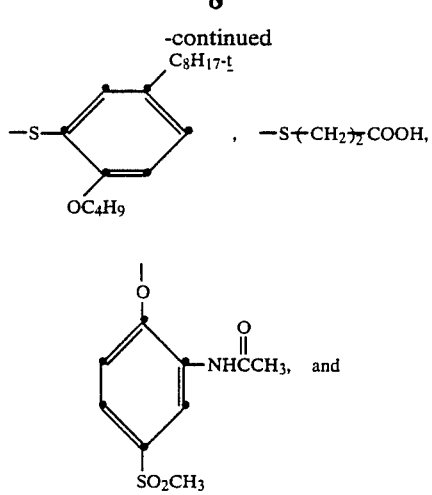

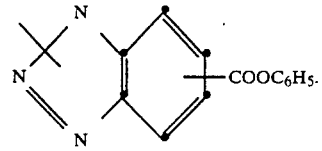

The pyrazoloazoles typically comprise a ballast group. A ballast group as described is an organic radical of such size and configuration as to confer on the coupler molecule sufficient bulk to render the coupler substantially non-diffusible from the layer in which it is coated in a photographic element. Couplers of the invention may be attached to ballast groups, or to polymeric chains through one or more of the groups on the pyrazoloazole nucleus. For example, one or more coupler moieties can be attached to the same ballast group. Representative ballast groups include substituted or unsubstituted alkyl or aryl groups containing 8 to 32 carbon atoms. Representative substituents include alkyl, aryl, alkoxy, aryloxy, alkylthio, arylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido, and sulfamoyl groups wherein the alkyl and aryl substituents and the alkyl and aryl portions of the alkoxy, aryloxy, alkylthio, arylthio, alkoxycarbonyl, arylcarbonyl, acyl, acyloxy, carbonamido, carboamoyl, alkylsulfonyl, arylsulfonyl, sulfonamido, and sulfamoyl substituents containing 1 to 30 carbon atoms and 6 to 30 carbon atoms, respectively, can be further substituted with such substituents.

Particularly useful pyrazoloazole couplers are those that comprise a water-solubilizing group for some photographic materials that enables increased reactivity of the coupler. For example, a particularly useful coupler is a pyrazoloazole, as described, comprising a substituent, such as a ballast group, comprising at least one carboxy group.

Particularly useful pyrazoloazole couplers are represented by the formula:

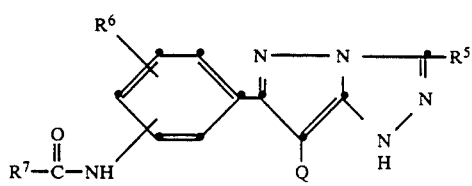

wherein

Q is hydrogen or a coupling-off group, preferably chlorine;

$R^5$ and $R^6$ are individually hydrogen or unsubstituted or substituted alkyl, alkoxy, aryl or aryloxy;

$R^7$ is a substituted or unsubstituted polyether group containing at least two ether (—O—) groups, preferably at least two ethyloxy groups [$+Ch_2CH_2O+_2$].

Other particularly useful couplers are those represented by the above formula wherein $R^5$ is optionally a substituted or unsubstituted polyether group containing at least two ether (—O—) groups, preferably at least two ethyloxy groups.

Illustrative pyrazoloazole couplers containing the linking group and polyether group as described are as follows:

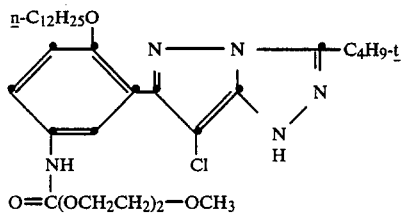

Compound 1

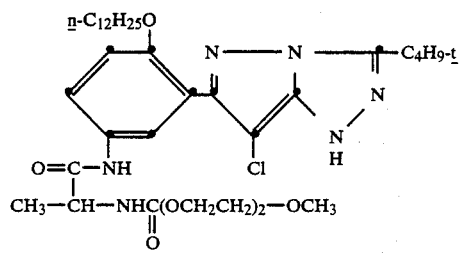

Compound 2

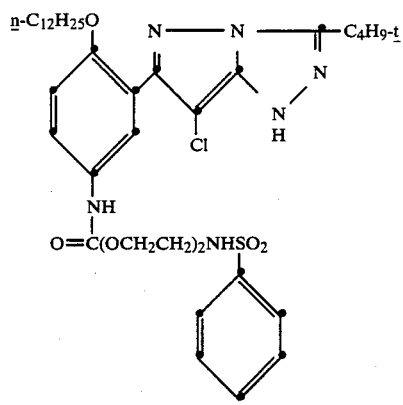

Compound 3

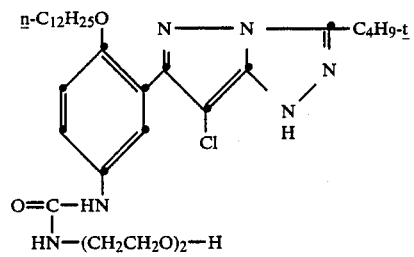

Compound 4

Compound 5
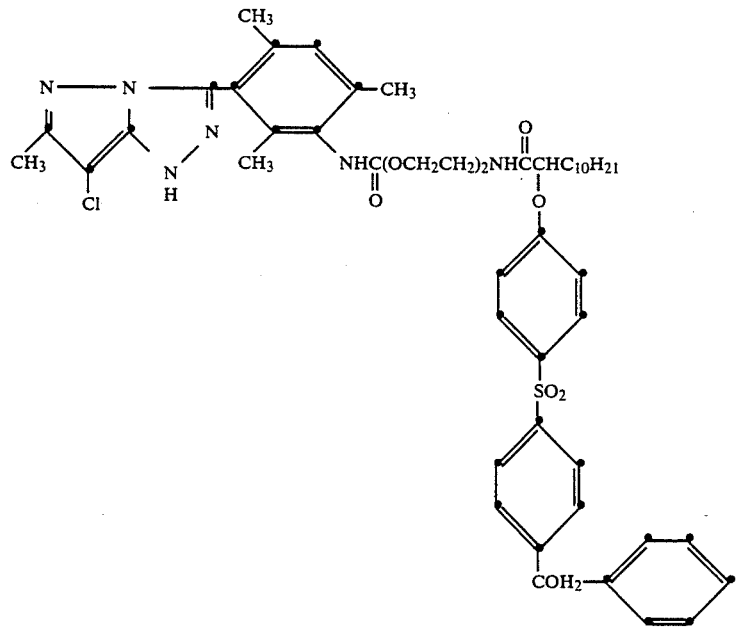
Compound 6
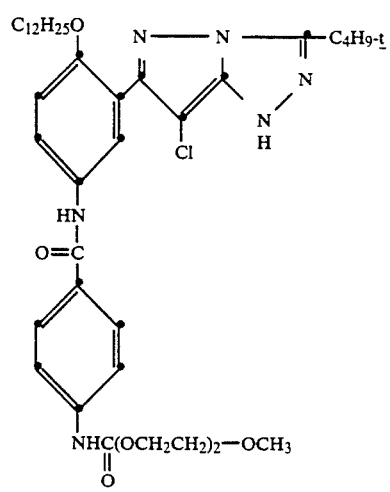
Compound 7
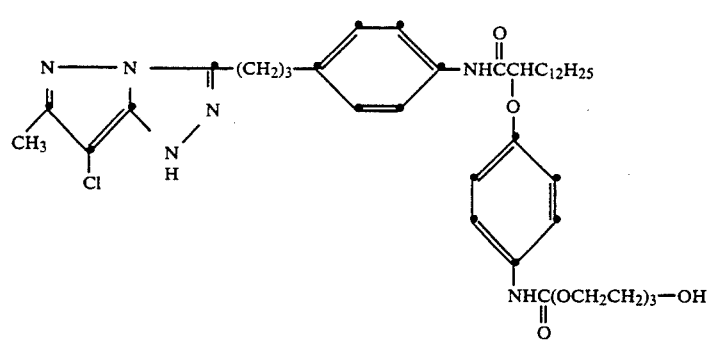
Compound 8
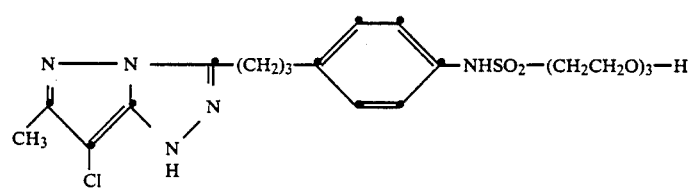

-continued

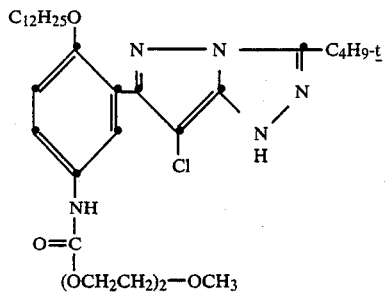
Compound 9

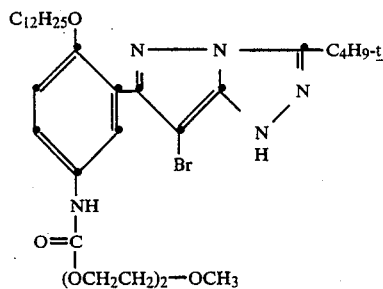
Compound 10

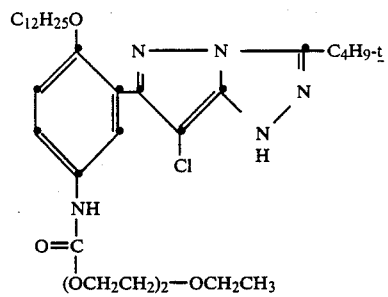
Compound 11

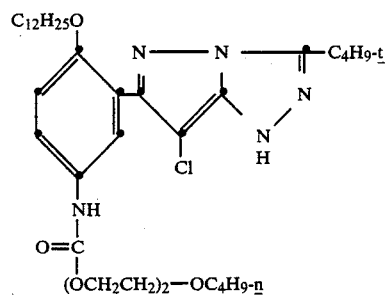
Compound 12

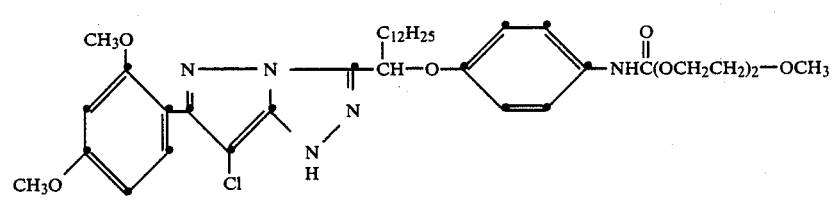
Compound 13

Pyrazoloazole couplers as described can be used in ways and for purposes that pyrazoloazole couplers have been used in the photographic art.

Pyrazolazole couplers as described, particularly pyrazolotriazole couplers, are prepared by general methods of synthesis described in the art, such as in *Research Disclosure*, Aug. 1974, Item No. 12443 published by Kenneth Mason Publications, Ltd., The Old Harbourmaster's 8 North Street, Emsworth, Hampshire P010 7DD, England and U.S. Pat. No. 4,540,654. An illustrative synthesis Scheme I is as follows:

Scheme I:

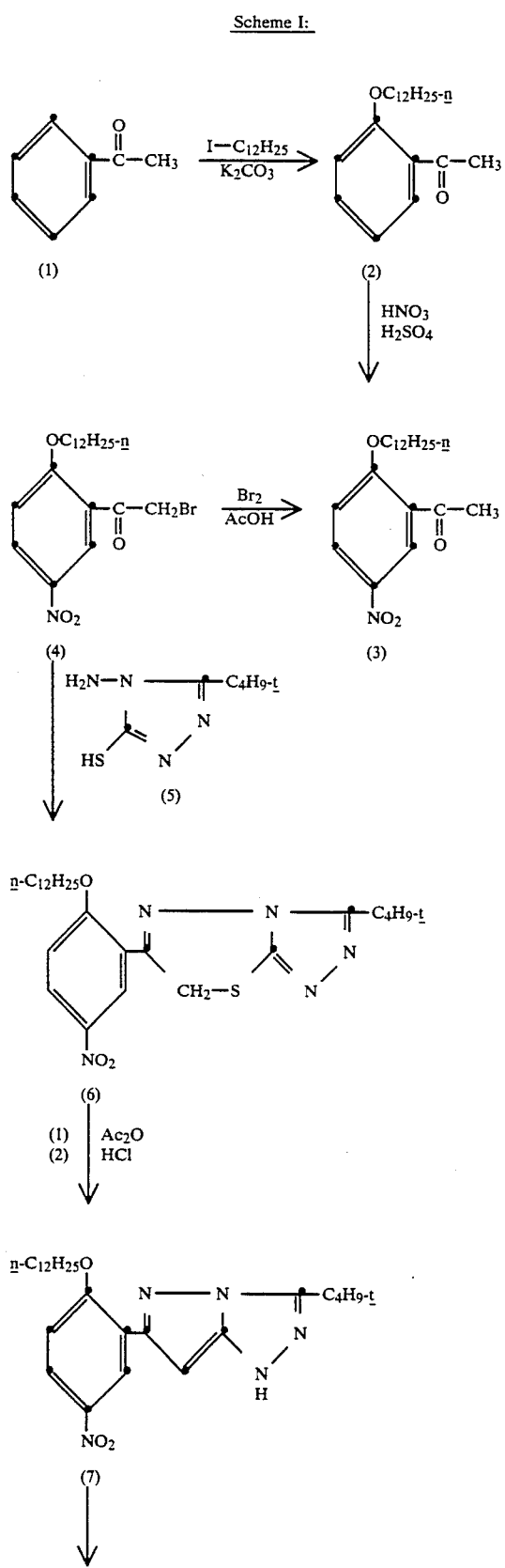

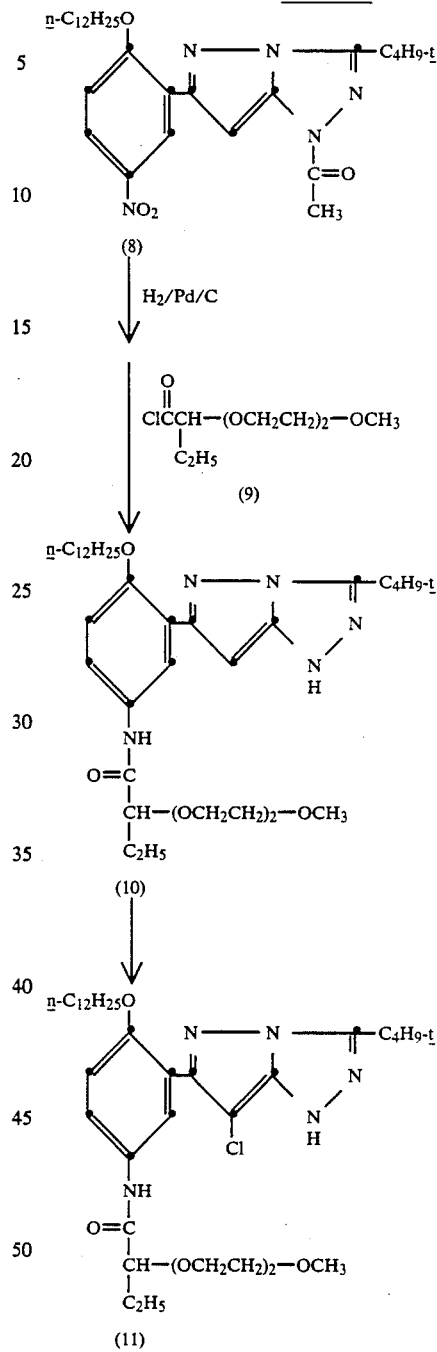

Examples of the synthesis of pyrazoloazole couplers as described are as follows:

SYNTHESIS EXAMPLE A

Synthesis of (2)

2'-Hydroxyacetophenone (136 g, 1.0 mol) was dissolved in 1000 ml of acetone and 100 ml of $H_2O$ and treated with 50% sodium hydroxide. A yellow solid is formed immediately and mechanical stirring is required. The iododocecane (296 g, 1.0 mol) is added in one portion and the reaction is heated at reflux with vigorous stirring for 2 days. All of the 2'-Hydroxyacetophenone was consumed by thin layer chromatography and only one new product was formed. The reaction was cooled to room temperature (20° C.) and partitioned with ligroin and water in a separatory funnel. The organic layer was washed with 10% NaOH twice and H₂O. The organic layer was dried (MgSO₄) and concentrated. The product was placed in the refrigerator at about 5° C. and crystallized. This material was collected and washed with methanol to form 205 g of the product (57%). More of the product was present in the mother liquors but was not recovered. The product (2) has an Mp of 29°-31° C.

Synthesis of (3)

Concentrated sulfuric acid (300 ml) was placed in a 2-liter erlenmeyer flask and cooled to 15° C. by an ice bath and stirred mechanically. The acetophenone compound (2) was added portionwise maintaining the solution below 25° C. The reaction was cooled to below 15° C. and the aqueous nitric acid (27 g of 70% HNO₃) was added dropwise with rapid stirring keeping the reaction temperature below 15° C. (Note that higher temperatures during the reaction promote the formation of the 3'-nitro-2-dodecyloxyacetophenone which is a minor side product of the reaction.) The addition required 2 hours. The reaction was poured slowly into 2 liters of ice keeping the reaction throughly cooled until throughly mixed with water. The mixture was extracted with ethyl acetate and the organic layer was washed with water and saturated NaHCO₃ and water again. The organic product was dried (MgSO₄) and concentrated to a dark oil. This material was taken up in 300 ml of ligroin and seeded with some solid and placed in a freezer at about −5° C. overnight. The solid was collected and washed with fresh cold ligroin and dried to give 66 g of product (3) (72%).

Synthesis of (4)

The 5'-nitro, 2'-dodecyloxyacetophenone (3) (76 g, 0.2 mol) was dissolved in 500 ml glacial acetic acid and neat bromine (35 g, 0.2 mol) was added dropwise over a 2-hour period, watching the temperature. The bromination appeared to generate no significant heat. After one equivalent of bromine was added the reaction was assumed complete because the products are hard to separate from the starting materials on thin layer chromatography. (Adding more bromine causes formation of the dibromoketone.) The reaction mixture was drowned out in water and extracted with ethyl acetate. The organic layer was washed with water and carefully washed with saturated NaHCO₃ several times to remove all the acetic acid. The organic product was dried (MgSO₄) and concentrated to yield a viscous yellow-brown oil. This product was carried on to the next step as is and was assumed to be complete for the next reaction.

Synthesis of (6)

The bromoketone (4) (85 g, 0.02 mol) and the aminothiodiazole (5) (38 g, 0.2 mol) were mixed in methanol (300 ml) and heated at reflux under nitrogen for 4–6 hours until reaction was complete by thin layer chromatography. The reaction was concentrated and 300 ml ethyl acetate was added and the mixture again concentrated. This procedure was repeated until a solid was formed from the dark colored mixture. This solid material was collected and washed with 600 ml diethyl ether. This white solid hydrobromide salt was dissolved in methanol/ethyl acetate and treated with 10% sodium hydroxide. The organic layer was dried (MgSO₄) and concentrated to a white solid (6) (Mp 114°-115° C.) (Yield 85 g. 77%).

Synthesis of (7)

The thiadiazine (6) (50 g, 0.1 mol) was dissolved in acetic anhydride (200 ml) and heated at reflux for 2 hours until the reaction was complete by thin layer chromatography. The reaction was allowed to cool to room temperature (20° C. ) and concentrated, removing ⅓ to ½ of the actic anhydride. Concentrated HCl (75 ml) was added with care. After the addittion of 20 ml of concentrated HCl a very exothermic reaction occurs as the acetic anhydride is hydrolyzed. The addition of concentrated HCl was done slowly until the acetic anhydride was consumed and the exothermic reaction ceased. The reaction composition was reheated to reflux for 2 hours and stirred overnight or until complete. The reaction was poured into 200 ml water and extracted with 200 ml ethyl acetate. The organic layer was washed with water and then cautiously with saturated NaHCO₃ until the water washed were basic. The organic layer was dried (MgSO₄) and concentrated to yield a yellow solid. This material was recrystallized twice from methanol filtering and the hot solution to remove sulfur to give 41 g of (7) (82% yield) (Mp 109°-110° C.).

Synthesis of (8)

The pyrazolotriazole (7) (40 g, 0.08 mol) was dissolved in tetrahydrofuran (200 ml) and treated with acetic anhydride (16 g, 0.16 mol) and pyridine (12 g, 0.16 mol) and heated at reflux for 24 hours. The reaction continued until complete by thin layer chromatography. The reaction was cooled to room temperature (20° C.) and partitioned between ethyl acetate (200 ml) and 10% HCl (200 ml). The organic layer was washed with 10% HCl (200 ml), dried and concentrated to yield a thick oil which was seeded and allowed to stand overnight. The crystalline solid was collected and recrystallized from acetonitrile to give a white solid (8) (32 g) (Mp 65°-66° C.).

Synthesis of 10

The nitro intermediate (8) (6 g, 0.0117 mol) was dissolved in tetrahydrofuran (50 ml) and treated with 2 g of 10% palladium on carbon and shaken with hydrogen overnight (the ease and time required for this reaction depends on the sulfur impurity carried from previous steps). The reaction was shown to be complete by thin layer chromatography and was filtered. The reaction was treated with N,N-dimethylaniline (1.5 g, 0.013 mol) and a solution of (9) (3 g, 0.013 mol) in 20 ml of tetrahydrofuran was added dropwise at room temperature (20° C.) and the reaction was stirred for 2 hours. The reaction was partitioned between ethyl acetate (200 ml) and 10% HCl (200 ml) and the organic was dried (MgSO₄) and concentrated. The residue was recrystallized from methanol to yield 5.8 g (10) (74%).

Synthesis of (11) from (10)

The pyrazolotriazole (10) (7 g, 0.01 mol) was dissolved in dichloromethane and treated with n-chlorosuccinimide (1.6 g, 0.012 mol) at room temperature (20° C.) for 3–6 hours. The chlorinated reaction was partitioned with H₂O containing L-ascorbic acid (5 g) and shaken well to reduce any excess n-chlorosuccinimide. The organic layer was collected and dried (MgSO$_4$) and concentrated. The residue was taken up in 75 ml of tetrahydrofuran and 75 ml of methanol and treated with 2 g of 50% sodium hydroxide and stirred at room temperature (20° C.) for 2 hours. The reaction was partitioned with ethyl acetate and 10% HCl and the organic layer was washed with H$_2$O, dried (MgSO$_4$) and concentrated. The solid which was obtained was recrystallized from cyclohexane to yield 4.7 g (11) (71%). The product (7) was identified by elemental and nmr analysis.

The couplers of this invention can be incorporated in silver halide emulsions and the emulsions can be coated on a support to form a photographic element. Alternatively, the couplers can be incorporated in photographic elements adjacent the silver halide emulsion where, during development, the coupler will be in reactive association with development products such as oxidized color developing agent.

The photographic elements can be either single color or multicolor elements. In a multicolor element, the magenta dye-forming coupler is usually associated with a green-sensitive emulsion, although they could be associated with an unsensitized emulsion or an emulsion sensitized to a different region of the spectrum. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprising at least one red-sensitive silver halide emulsion layer having associated therewith at least one cyan dye-forming coupler, a magenta image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler. The element can contain additional layers, such as filter layers, inter-layers, overcoat layers, subbing layers, and the like.

In the following discussion of suitable materials for use in the elements of this invention, reference will be made to *Research Disclosure*, Dec. 1978, Item 17643, published by Kenneth Mason Publications, Ltd., The Old Harbourmaster's, 8 North Street, Emsworth, Hampshire PO10 7DD, ENGLAND, the disclosures of which are incorporated herein by reference. This publication will be identified hereafter by the term "*Research Disclosure.*"

The silver halide emulsions employed in the elements of this invention can be comprised of silver bromide, silver chloride, silver iodide, silver chlorobromide, silver chloroiodide, silver bromoiodide, silver chlorobromoiodide or mixtures thereof. The emulsions can include silver halide grains of any conventional shape or size. Specifically, the emulsions can include coarse, medium or fine silver halide grains. High aspect ratio tabular grain emulsions are specifically contemplated, such as those disclosed by Wilgus et al U.S. Pat. No. 4,434,226, Daubendiek et al U.S. Pat. No. 4,414,310, Wey U.S. Pat. No. 4,399,215, Solberg et al U.S. Pat. No. 4,433,048, Mignot U.S. Pat. No. 4,386,156, Evans et al U.S. Pat. No. 4,504,570, Maskasky U.S. Pat. No. 4,400,463, Wey et al U.S. Pat. No. 4,414,306, Maskasky U.S. Pat. Nos. 4,435,501 and 4,643,966 and Daubendiek et al U.S. Pat. Nos. 4,672,027 and 4,693,964. Also specifically contemplated are those silver bromoiodide grains with a higher molar proportion of iodide in the core of the grain than in the periphery of the grain, such as those described in GB No. 1,027,146; JA No. 54/48,521; U.S. Pat. No. 4,379,837; U.S. Pat. No. 4,444,877; U.S. Pat. No. 4,665,012; U.S. Pat. No. 4,686,178; U.S. Pat. No. 4,565,778; U.S. Pat. No. 4,728,602; U.S. Pat. No. 4,668,614; U.S Pat. No. 4,636,461; EP No. 264,954. The silver halide emulsions can be either monodisperse or polydisperse as precipitated. The grain size distribution of the emulsions can be controlled by silver halide grain separation techniques or by blending silver halide emulsions of differing grain sizes.

Sensitizing compounds, such as compounds of copper, thallium, lead, bismuth, cadmium and Group VIII noble metals, can be present during precipitation of the silver halide emulsion.

The emulsions can be surface-sensitive emulsions, i.e., emulsions that form latent images primarily on the surfaces of the silver halide grains, or internal latent image-forming emulsions, i.e., emulsions that form latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

The silver halide emulsions can be surface sensitized. Noble metal (e.g., gold), middle chalcogen (e.g., sulfur, selenium, or tellurium), and reduction sensitizers, employed individually or in combination, are specifically contemplated. Typical chemical sensitizers are listed in *Research Disclosure*, Item 17643, cited above, Section III.

The silver halide emulsions can be spectrally sensitized with dyes from a variety of classes, including the polymethine dye class, which includes the cyanines, merocyanines, complex cyanines and merocyanines (i.e., tri-, tetra-, and poly-nuclear cyanines and merocyanies), oxonols, hemioxonols, styryls, merostyryls, and streptocyanines. Illustrative spectral sensitizing dyes are disclosed in *Research Disclosure*, Item 17643, cited above, Section IV.

Suitable vehicles for the emulsion layers and other layers of elements of this invention are described in Research Disclosure Item 17643, Section IX and the publications cited therein.

In addition to the couplers described herein the elements of this invention can include additional couplers as described in Research Disclosure Section VII, paragraphs D, E, F and G and the publications cited therein. These additional couplers can be incorporated as described in Research Disclosure Section VII, paragraph C and the publications cited therein.

The photographic elements of this invention can contain brighteners (Research Disclosure Section V), antifoggants and stabilizers (Research Disclosure Section VI), antistain agents and image dye stabilizers (Research Disclosure Section VII, paragraphs I and J), light absorbing and scattering materials (Research Disclosure Section VIII), hardeners (Research Disclosure Section X), coating aids (Research Disclosure Section XI), plasticizers and lubricants (Research Disclosure Section XII), antistatic agents (Research Disclosure Section XIII), matting agents (Research Disclosure Section XVI) and development modifiers (Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-β-(methanesulfonamido)ethylaniline sulfate hydrate, 4-amino-3-methyl-N-ethyl-N-β-hydroxyethylaniline sulfate, 4-amino-3-β-(methanesulfonamido)ethyl-N,N-diethylaniline hydrochloride and 4-amino-N-ethyl-N-(2-methoxyethyl)-m-toluidine di-p-toluene sulfonic acid.

With negative-working silver halide, the processing step described above provides a negative image. The described elements are preferably processed in the known C-41 color process as described in, for example, the British Journal of Photography Annual of 1982, pages 209–211. To provide a positive (or reversal) image, the color development step can be preceded by development with a non-chromogenic developing agent to develop exposed silver halide, but not form dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver or silver halide, washing, and drying.

The following examples further illustrate the invention.

EXAMPLE 1

(Photographic Elements Comprising Pyrazoloazole Couplers of the Invention)

Photographic elements were prepared by coating a cellulose acetate-butyrate film support with a photosensitive layer containing a silver bromoiodide emulsion at 0.91 gm Ag/m$^2$, gelatin at 3.77 gm/m$^2$, and one of the couplers designated in Table I dispersed in half its weight of tricresyl phosphate and coated at 1.62 mmol/m$^2$. The photosensitive layer was overcoated with a layer containing gelatin at 1.08 gm/m$^2$ and bis-vinylsulfonylmethyl ether at 1.75 weight percent based on total gelatin.

Samples of each element were imagewise exposed through a graduated-density test object and processed at 40° C. employing the following color developing solution, then stopped, bleached, fixed, washed, and dried to produce stepped magenta dye images.

| | |
|---|---|
| K$_2$SO$_3$ | 2.0 gm |
| K$_2$CO$_3$ | 30.0 gm |
| KBr | 1.25 gm |
| KI | 0.6 mg |
| 4-amino-3-methyl-N-ethyl-N-B'-hydroxy-ethylaniline sulfate | 3.55 gm |
| Water to 1.0 liter, pH 10.0 | |

The produced magenta dye images were evaluated as shown in Table I. Densitometry of these images provided measures of maximum density (D$_{max}$) (measure of activity).

TABLE I

| Coupler No. | Dmax (measure of activity) |
|---|---|
| Compound A | 1.54 |
| No. 1 | 2.70 |
| No. 2 | 2.56 |

Compound A

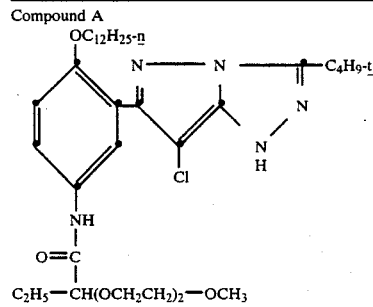

$C_2H_5$—CH(OCH$_2$CH$_2$)$_2$—OCH$_3$

The couplers of the invention provide improved photographic activity.

The invention has been described in detail with particular reference to preferred embodiments thereof, but it will be understood that variations and modifications can be effected within the spirit and scope of the invention.

What is claimed is:

1. A photographic element comprising a support bearing a photographic silver halide emulsion and a dye-forming coupler wherein the dye-forming coupler is a pyrazoloazole coupler comprising (I) at least one polyether group (A) comprising at least two ether (—O—) groups and (II) having between the group (A) and the pyrazoloazole nucleus a linking group wherein the pyrazoloazole coupler is represented by the formula:

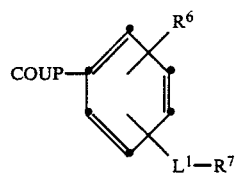

wherein
COUP is a pyrazoloazole coupler nucleus;
R$^6$ is hydrogen or unsubstituted or substituted alkyl, aryl, alkoxy or aryloxy;
L$^1$ is

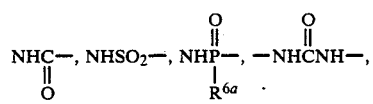

-continued

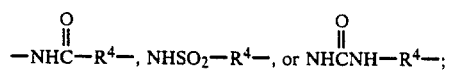, NHSO$_2$—R$^4$—, or ;

where the second group is:

—NHC(=O)—R$^4$—, NHSO$_2$—R$^4$—, or NHC(=O)NH—R$^4$—;

R$^4$ is unsubstituted or substituted alkylene;

R$^{6a}$ is R$^6$ or O—R$^7$; and

R$^7$ is a polyether group.

2. A photographic element as in claim 1 wherein the polyether group (A) is terminated by a water solubilizing group.

3. A photographic element as in claim 1 wherein the pyrazoloazole coupler is represented by the formula:

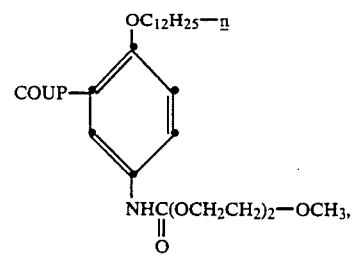

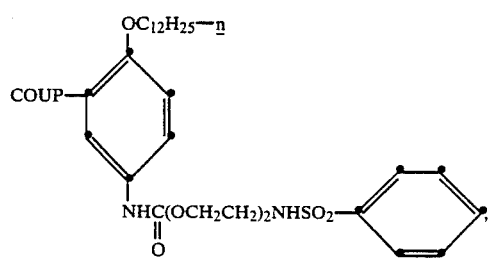

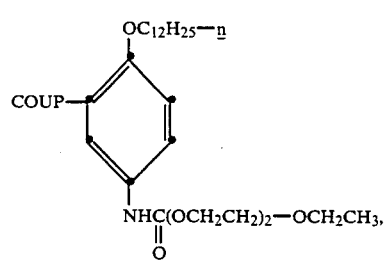

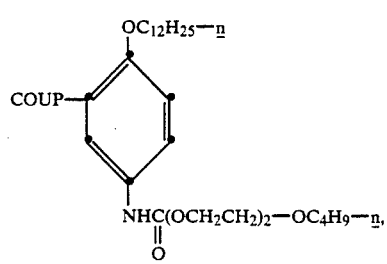

-continued

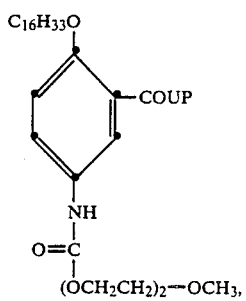

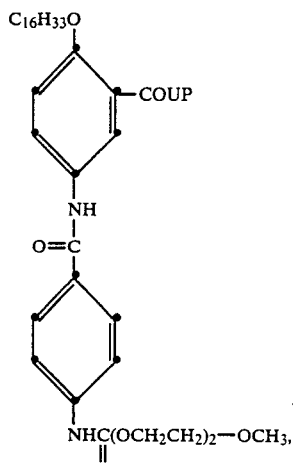

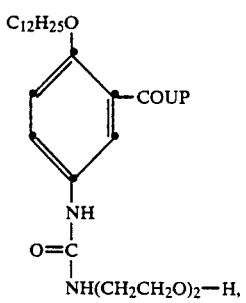

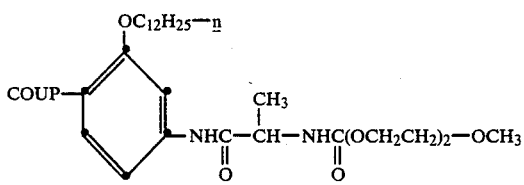

wherein COUP is a pyrazoloazole coupler nucleus.

4. A photographic element as in claim 1 wherein the pyrazoloazole coupler is a pyrazolo[3,2-c]-s-triazole represented by the formula:

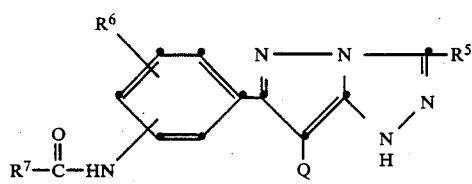

wherein

Q is hydrogen or a coupling-off group;

$R^5$ is hydrogen or unsubstituted or substituted alkyl or aryl;

$R^6$ is hydrogen or unsubstituted or substituted alkyl, alkoxy, aryl or aryloxy; and $R^7$ is a substituted or unsubstituted polyether group containing at least two ether (—O—) groups.

5. A photographic element as in claim 1 wherein the pyrazoloazole coupler is selected from the group consisting of:

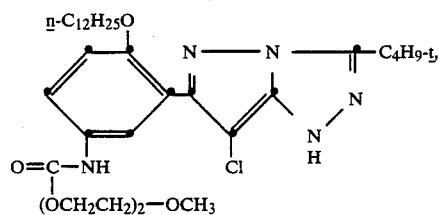

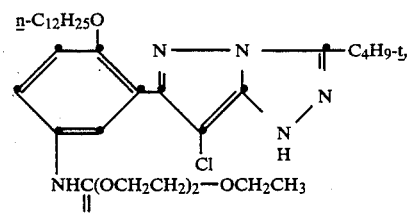

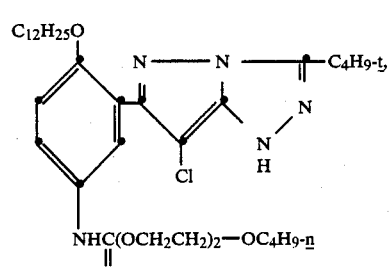

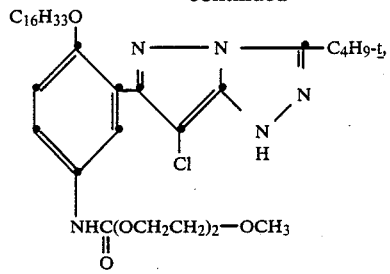

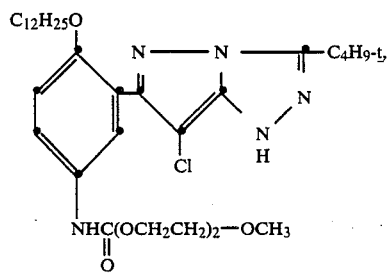

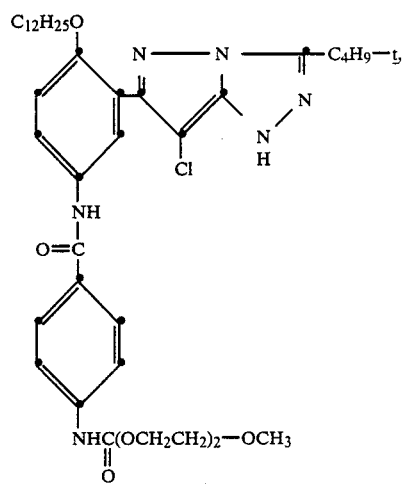

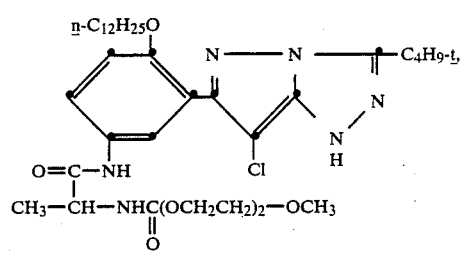

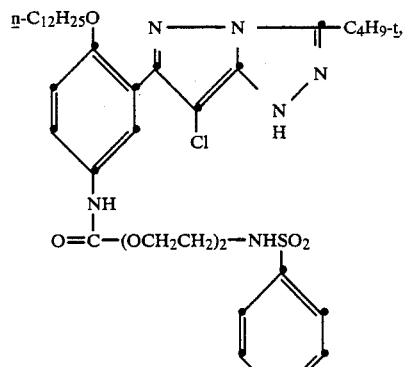

and

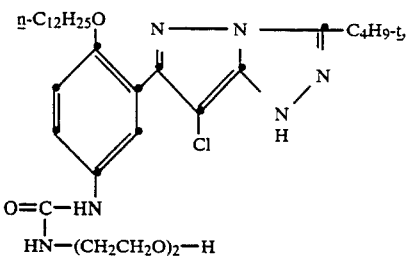

6. A process of forming a dye image in an exposed photographic element comprising a support bearing a photographic silver halide emulsion, said process comprising developing the photographic element with a silver halide color developing agent in the presence of a color coupler comprising a pyrazoloazole coupler as defined in claim 1.

7. A process as in claim 6 wherein the pyrazoloazole is a pyrazolo[3,2-c]-s-triazole represented by the formula:

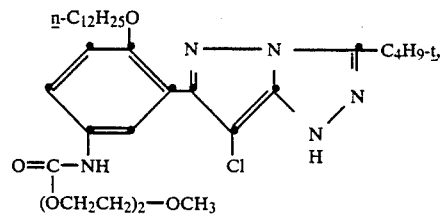

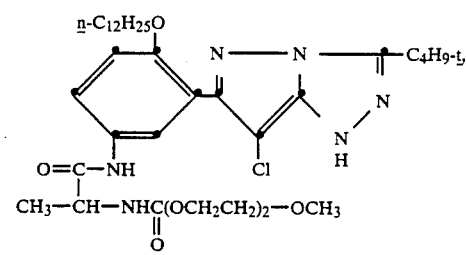

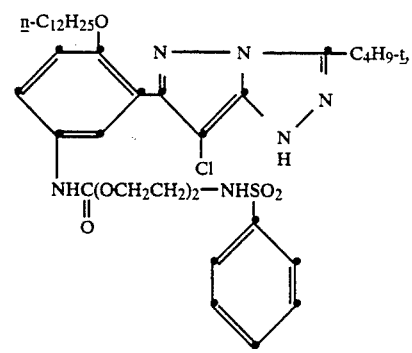

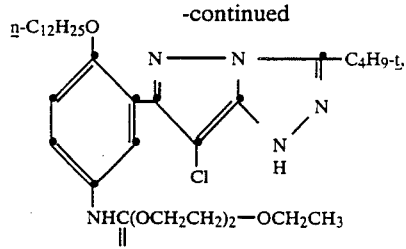

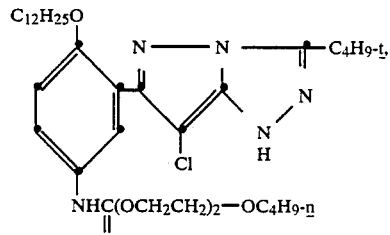

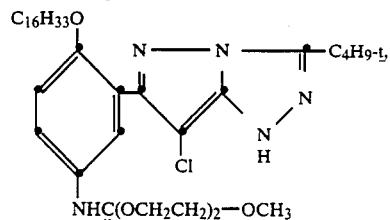

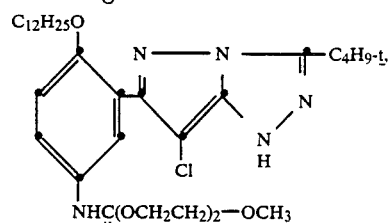

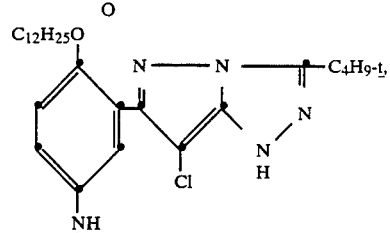

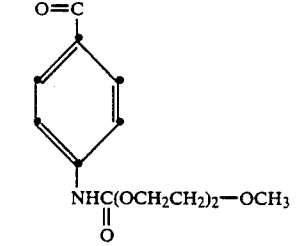

and

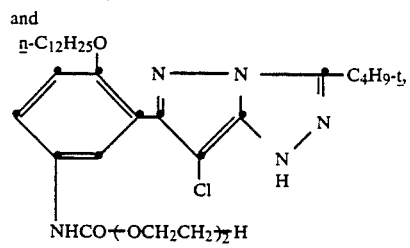

* * * * *